United States Patent [19]

Hirai et al.

[11] 4,405,737
[45] Sep. 20, 1983

[54] N-2-HYDROXYPROPYL PIPERIDINES AND COMPOSITIONS THEREOF

[75] Inventors: Bunji Hirai, Kuki; Naohiro Kubota, Ageo; Kazuo Sugibuchi, Tokyo, all of Japan

[73] Assignee: Adeka Argus Chemical Co., Ltd., Urawa, Japan

[21] Appl. No.: 346,424

[22] Filed: Feb. 5, 1982

[30] Foreign Application Priority Data

Feb. 17, 1981 [JP] Japan .............................. 56-22039

[51] Int. Cl.³ ...................... C08K 5/45; C07D 211/22
[52] U.S. Cl. ..................................... 524/102; 524/99; 252/403; 252/404; 252/405; 546/19; 546/186; 546/188; 546/190; 546/191; 546/216; 546/240; 546/242; 546/248
[58] Field of Search ................. 546/19, 186, 188, 190, 546/191, 216, 240, 242, 248; 524/99, 102; 252/403, 404, 405

[56] References Cited
FOREIGN PATENT DOCUMENTS 1695765 1/1973 Fed. Rep. of Germany ...... 546/240

*Primary Examiner*—Robert T. Bond

[57] ABSTRACT

N-2-Hydroxypropyl piperidines are provided, as well as a process for preparing these compounds, having the formula:

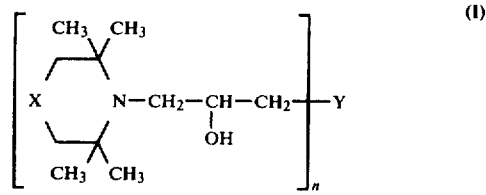

wherein X is selected from the group consisting of,

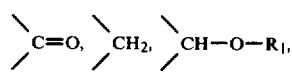

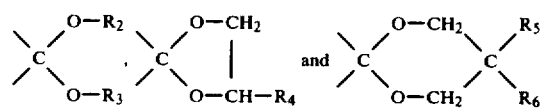

wherein
$R_1$ is selected from the group consisting of hydrogen; alkyl; alkenyl; cycloalkyl; alkaryl; hydroxyalkyl; oxyalkyl; acyl and aroyl having from one to about eighteen carbon atoms;
$R_2$ and $R_3$ are each selected from the group consisting of alkyl, alkenyl, cycloalkyl, alkaryl, hydroxyalkyl, oxyalkyl and haloalkyl having from one to about eighteen carbon atoms;
$R_4$, $R_5$ and $R_6$ each are selected from the group consisting of hydrogen, alkyl, alkenyl, cycloalkyl, alkaryl, hydroxyalkyl, oxyalkyl and haloalkyl having from one to about eighteen carbon atoms; and —$CH_2$—O—$R_1$;
n is 1 or 2; and
Y, when n is 1, is hydroxy or

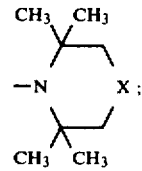

and when n is 2, is oxyoxygen.

35 Claims, No Drawings

N-2-HYDROXYPROPYL PIPERIDINES AND COMPOSITIONS THEREOF

Hindered 2,2,6,6-tetraalkyl-4-carboxylic acid ester piperidine compounds having been proposed by Murayama et al U.S. Pat. No. 3,640,928, patented Feb. 8, 1972 as light and heat stabilizers for synthetic polymers, such as polyolefins, polyvinyl chloride, polyvinylidene chloride, polyurethanes, and polyamides. These compounds have the general formula:

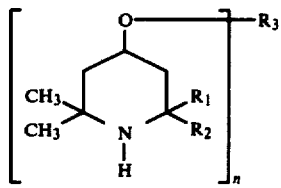

or a salt thereof.

In the above formula:

$R_1$ and $R_2$ which may be the same or different, each are an alkyl group such as methyl, ethyl, isopropyl or dodecyl, or they form, together with the carbon atom to which they are attached, a saturated alicyclic group such as:

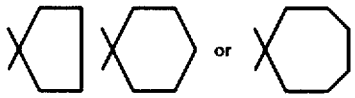

or a group of the formula

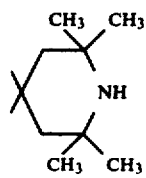

n is an integer of 1 to 3 inclusive; and
$R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al patent has been followed by a large number of patent and literature disclosures by Murayama et al and others of compounds including a 2,2,6,6-tetrasubstituted-4-piperidyl group attached to a base molecule of varying structures.

Murayama et al U.S. Pat. No. 3,898,303 patented Aug. 5, 1975 propose piperidino-spiro-hydantoin derivatives having the formula:

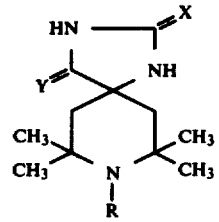

wherein: R represents an alkyl group, an alkenyl group, an alkenoyl group which may be substituted with an aryl group, a hydroxyalkyl group, an alkoxy-alkyl group, an alkoxycarbonylalkyl group, an acyloxyalkyl group, a cyanoalkyl group or nitroso group, and X and Y individually represent oxygen atom or sulfur atom.

Murayama et al in U.S. Pat. No. 3,899,464 patented Aug. 12, 1975 discloses a variation of the piperidino spiro compounds having the formula:

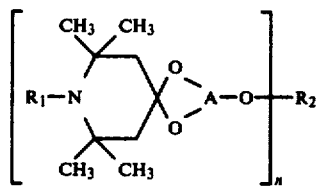

wherein:

$R_1$ represents hydrogen atom, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, n is an integer of 1 to 4;

when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, a N-substituted carbamoyl group, a N-substituted thiocarbamoyl group, a monovalent group from an oxoacid or group

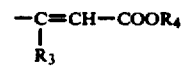

in which $R_3$ represents hydrogen atom, a lower alkyl group or phenyl group and $R_4$ represents an alkyl group;

when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid;

when n is 3, $R_2$ represents an aromatic triacyl group or a trivalent group from an oxoacid; and when n is 4, $R_2$ represents an aromatic tetraacyl group, and A represents a group

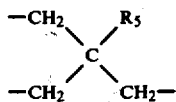

in which

R₅ represents hydrogen atom or a lower alkyl group or, when n is 1, R₅ may represent together with R₂ a group

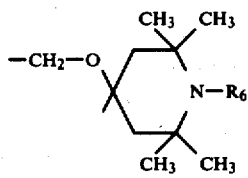

in which

R₆ represents the same group as defined in R₄ and may be the same or different from R₁, or a group

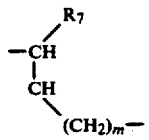

in which m is 1 or 2 and R₇ represents hydrogen atom or, when n and m are 1, R₇ represents methylene group together with R₂.

Murayama et al U.S. Pat. No. 3,840,494, patented Oct. 8, 1974 provides acid esters of 4-piperidonol derivatives having the formula:

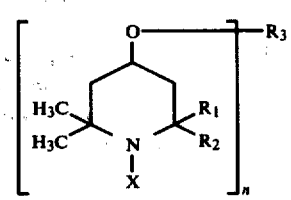

wherein

R₁ and R₂ may be the same or different and represent an alkyl group of one to four carbon atoms or they may form, together with the carbon atom to which they are attached, a saturated alicyclic group or the group of the formula:

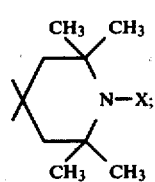

X is hydrogen atom, oxygen free radical (—O) or an alkyl group of one to four carbon atoms;

n is an integer of 1 through 4 inclusive; and R₃ represents, when n is 1, an acyl group derived from aliphatic or aromatic monocarboxylic acid, when n is 2, a diacyl group derived from an aliphatic or aromatic dicarboxylic acid or carbonyl group, when n is 3 a triacyl group derived from an aliphatic or aromatic tricarboxylic acid or a trivalent group obtained by eliminating three hydroxyl groups from phosphoric acid, phosphorous acid or boric acid, and when n is 4, a tetraacyl group derived from an aromatic tetracarboxylic acid or a tetravalent group obtained by eliminating four hydroxyl groups from orthosilicic acid.

Murayama et al U.S. Pat. No. 3,933,735 patented Jan. 20, 1976 propose 4-piperidone derivatives having a structure similar to the 4-piperidyl derivatives, but with a keto oxygen at the 4-position of the piperidine ring.

Murayama et al U.S. Pat. No. 3,941,744 patented Mar. 2, 1976, disclose another variation of the piperidino spiro derivatives having the formula:

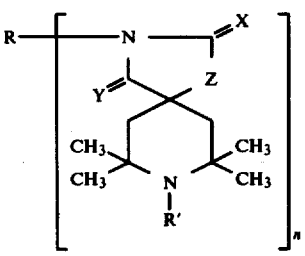

wherein

R' represents an alkyl group, a substituted alkyl group, an acyl group, an alkoxycarbonyl group, a substituted alkoxycarbonyl group, an amino group, a substituted amino group or nitroso group;

X represents oxygen atom or sulfur atom;

Y represents oxygen atom, sulfur atom or a group of the formula =N—R" in which R" is hydrogen atom, an alkyl group or a substituted alkyl group;

Z represents oxygen atom or a group of the formula >N—R'" is hydrogen atom, an alkyl group or a substituted alkyl group;

n is an integer of 1 through 4 inclusive; and

R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group, when n is 2, an alkylene group, an alkenylene group, an arylene group, a substituted arylene group, an aralkylene group, an alkylenediphenylene group, a bis-(acyloxyalkylene)group, an alkylene-bis-(oxycarbonylalkyl) group, a dialkylene ether group or a diphenylene ether group, when n is 3, an alkanetriyl group, a tris-(acyloxyalkylene) group, an alkane-tris-(oxycarbonylalkyl) group or a group of the group

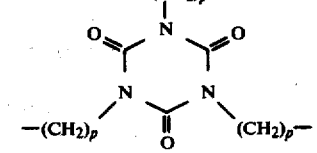

in which p is an integer of 1 through 8 inclusive, and when n is 4, an alkane tetrayl group, a tetrakis-(acyloxyalkylene) group or an alkanetetrakis-(oxycarbonylalkyl) group.

Murayama et al U.S. Pat. No. 3,940,363 patented Feb. 24, 1976 disclose a further variation in which two 2,2,6,6-tetrasubstituted-4-piperidyl groups are linked together via the ring nitrogen atom to an R' alkylene linking group, which may be interrupted with an oxygen or sulfur atom, an alkenylene group, an alkynylene group, an aralkylene group, an aliphatic diacyl group, a group having the formula:

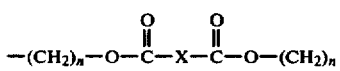

in which n is an integer of 1 or 2 and X is an alkylene group, or o-, m- or p-phenylene group or the carbon atoms of CO groups may be directly joined in the absence of X or a group of the formula:

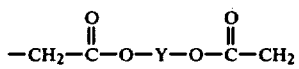

in which Y is an alkylene group or o-, m- or p-phenylene group.

Ramey et al U.S. Pat. Nos. 3,907,803 patented Sept. 23, 1975 and 4,001,181 patented Jan. 4, 1977 provide hindered piperidine carboxamide acids and metal salts thereof of the formula:

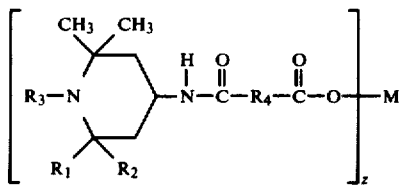

wherein
R$_1$ and R$_2$ independently of each other are straight- or branched-chain lower alkyl having from one to six carbon atoms, or together with the carbon to which they are bound form a cyclopentyl or cyclohexyl ring, which is unsubstituted or substituted with a methyl group, R$_3$ is hydrogen, alkyl having from one to twelve carbon atoms, β-methoxyethyl alkenyl having three or four carbon atoms, propargyl, benzyl, or alkyl-substituted benzyl, R$_4$ is straight- or branched-chain alkylene having one to eight carbon atoms, phenylene, phenylene substituted with one or more alkyl groups, or the group —(CH$_2$)$_m$Y(CH$_2$)$_n$—, wherein Y is oxygen or sulfur and m and n independently of each other are an integer of from 1 to 3, M is hydrogen or a metal selected from the group consisting of barium, nickel, manganese, calcium, zinc, iron, sodium, cobalt, tin, and dialkyl tin, and z has a value of from 1 to 4, the value of z being the same as the available valance of M.

Ramey et al U.S. Pat. No. 3,920,661 patented Nov. 18, 1975 disclose dicarboxylic acids and salts in which one carboxylic acid group is esterified with a 2,2,6,6-tetrasubstituted-4-hydroxy piperidine and having the formula:

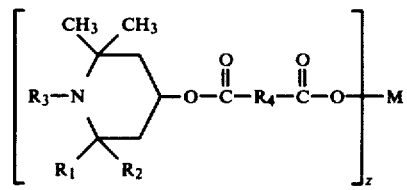

wherein
R$_1$ and R$_2$ independently of each other are straight- or branched-chain alkyl having from one to six carbon atoms, or together with the carbon to which they are bound form a cyclopentyl or cyclohexyl ring, which is unsubstituted or substituted with a methyl group;

R$_3$ is hydrogen, alkyl having from one to twelve carbon atoms, β-methoxyethyl, alkenyl having three or four carbon atoms, propargyl, benzyl or alkyl-substituted benzyl;

R$_4$ is straight or branched-chain alkylene having five to eight carbon atoms, or the group (CH$_2$)$_m$Y(CH$_2$)$_n$ wherein Y is oxygen or sulfur and m and n independently of each other are an integer from 1 to 3;

M is hydrogen or a metal selected from the group consisting of barium, nickel, manganese, calcium, zinc, iron, sodium, cobalt, tin, and dialkyl tin, and z has a value of from 1 to 4, the value of z being the same as the available valence of M.

Ramey et al U.S. Pat. No. 3,939,163 patented Feb. 17, 1976 disclose closely similar compounds in which R$_4$ is alkylene having from one to four carbon atoms.

Randell et al U.S. Pat. No. 3,939,170 patented Feb. 17, 1976 disclose dehydropyridinyl sulfides, sulfoxides and sulfones having the formula:

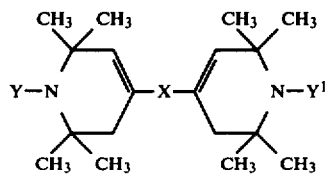

wherein X is S, SO or SO$_2$ and Y and Y$^1$ are the same or different and each is H, OH, O— or a straight- or branched alkyl residue having from one to four carbon atoms, and salts thereof when Y and Y$^1$ are other than O—.

Randell et al in published patent application Ser. No. B408,123 published Apr. 13, 1976 disclose substituted piperidine-4-ols having the formula:

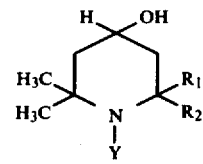

wherein R$_1$ and R$_2$ are the same or different and each is a straight- or branched alkyl residue having from one to twelve carbon atoms, or R$_1$ and R$_2$, together with the carbon atom to which they are attached, form a cycloalkyl residue having from five to twelve carbon atoms or the group:

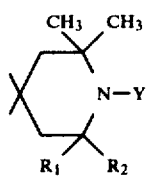

wherein R₁ and R₂ have their previous significance and Y is a straight- or branched alkyl residue having from one to twenty carbon atoms, an alkenyl or alkynyl residue having from three to twenty carbon atoms, an aralkyl residue having from seven to twelve carbon atoms or the group —CH₂X wherein X is the group

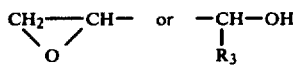

wherein R₃ is hydrogen, a methyl or phenyl residue, the group

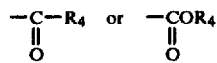

wherein R₄ is an alkyl residue having from one to twenty carbon atoms.

Cook U.S. Pat. No. 3,929,804 patented Dec. 30, 1975 discloses 4-piperidine acetamide compounds having the formula:

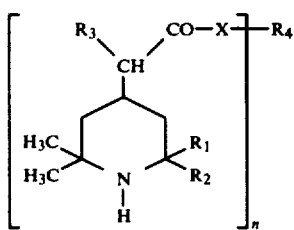

wherein
R₁ and R₂ are the same or different and each is a straight-or branched alkyl residue having from one to twelve carbon atoms, or R₁ and R₂, together with the carbon atom to which they are attached form a cycloalkyl group having from five to twelve carbon atoms;
R₃ is hydrogen, a straight-or branched alkyl residue having from one to four carbon atoms, an aralkyl residue having from seven to nine carbon atoms or a cycloalkyl group having from five or six carbon atoms;
R₄ is a metal ion or a hydrocarbyl residue having from two to twenty carbon atoms and being either unsubstituted or substituted by halogen or interrupted by one or more oxygen or sulphur atoms;
X is —O—, —S—, or >NR₅, wherein R₅ has the same significance as R₃; and
n is 2, 3 or 4;
as well as salts of the amine function of the compounds of formula I.

Cook U.S. Pat. No. 3,939,168 patented Feb. 17, 1976 discloses closely similar compounds having a Y substituent on the piperidyl nitrogen atom, Y being alkyl, alkenyl, aralkyl or a group

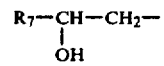

wherein R₇ is hydrogen, alkyl or phenyl.

Cook U.S. Pat. No. 3,959,291, patented May 25, 1976 provides derivatives of substituted 2-piperidinyl-4'-ethyl alcohol having the formula:

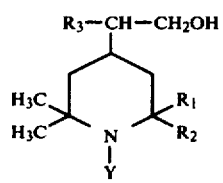

and salts thereof, wherein
R₁ and R₂ are the same or different and each is an alkyl residue having from one to twelve carbon atoms, or R₁ and R₂, together with the carbon atom to which they are bound, form a cycloalkyl residue having from five to twelve carbon atoms in the ring;
Y is O, hydrogen, a straight- or branched-alkyl residue having from one to twenty carbon atoms, an alkenyl or alkynyl residue having from three to twelve cabon atoms, an aralkyl residue having from seven to twelve carbon atoms or a group having the formula:

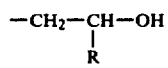

wherein
R is hydrogen, or a methyl or phenyl residue, and
R₃ is hydrogen, or a straight- or branched-chain alkyl residue having from one to twelve carbon atoms.

Cook U.S. Pat. No. 3,971,795, patented July 27, 1976 provides N-substituted piperidinylidene derivatives having the formula:

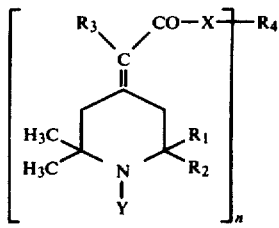

wherein
n is 1, 2, 3 or 4,
Y is hydrogen or a straight- or branched-alkyl residue having from one to twelve carbon atoms, an alkenyl residue having from three to twelve carbon atoms or an aralkyl residue having from seven to twelve carbon atoms and R₁ and R₂ are the same or different and each is a straight- or branched-alkyl residue having from one to twelve carbon atoms, or $R_1$ and $R_2$ together with the carbon atom to which they are attached form a cycloalkyl group having from five to twelve carbon atoms;

$R_3$ is hydrogen, a straight- or branched-alkyl residue having from one to four carbon atoms, an aralkyl residue having from seven to twelve carbon atoms, a cycloalkyl group having five or six carbon atoms;

$R_4$ is a hydrocarbyl residue having from one to twenty carbon atoms being either unsubstituted or substituted by halogen, or interrupted by one or more oxygen or sulphur atoms or $R_4$ is a metal ion, or, when n is 1, $R_4$, in addition, is hydrogen or has the structure:

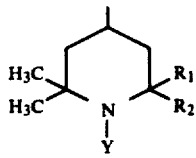

wherein
Y, $R_1$ and $R_2$ have their previous significance,
X is —O—, —S— or >$NR_5$ wherein
$R_5$ has the same significance as $R_3$ or when n is 1 in addition $R_5$ and $R_4$ together with the nitrogen atom to which they are bound form a heterocyclic residue having from four to ten carbon atoms;
as well as salts of the amine function of the compound of formula I.

Murayama et al U.S. Pat. No. 3,975,357, patented Aug. 17, 1976 provides 1-substituted piperidine derivatives having the formula:

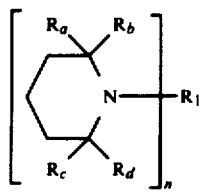

In the above formula, n represents 1 or 2.
$R_1$ represents when n=1, oxyl radical, hydroxy group, an alkyl group, a substituted alkyl group, an alkenyl group, an alkynyl group, an aralkyl group, a substituted aralkyl group or an acyl group,
when n=2, an alkylene group (the alkylene chain may optionally be interrupted by an oxygen atom), 2-butenylene group, a group of the formula —CH$_2$COO—R$_7$—O—COCH$_2$— wherein
$R_7$ represents an alkylene group or xylylene group, or a group of the formula —CH$_2$CH$_2$—OCO—R$_8$)$_m$COO—CH$_2$CH$_2$— wherein
m represents 0 or 1,
$R_8$ represents an alkylene group (the alkylene chain may optionally be interrupted by a sulfur atom), an alkenylene group, phenylene group or 1,4-cyclohexylene group.
$R_a$ and $R_b$ represent methyl group or $R_a$ and $R_b$ together with carbon atom to which they are attached, form cyclohexyl group.
$R_c$ represents methyl group.
$R_d$ represents an alkyl group having one to five carbon atoms.

$R_c$ and $R_d$ together with carbon atom to which they are attached, may form cyclopentyl group, cyclohexyl group, a group of the formula:

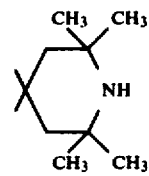

or a group of the formula

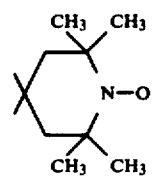

Minagawa et al, U.S. Pat. No. 4,222,931, patented Sept. 16, 1980, provides stabilizers for organic polymeric materials, comprising a phosphonic acid ester, a phenolic antioxidant and a 2,2,6,6-tetramethyl-4-piperidyl ether alcohol or ether having the general formula:

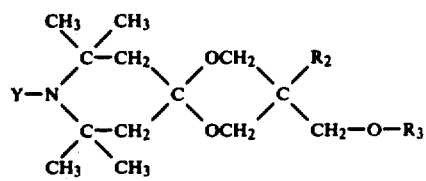

wherein
$R_2$ is lower alkyl or hydroxy alkyl having from one to six carbon atoms;
$R_3$ is a hydrogen atom, provided $R_2$ is hydroxyalkyl;

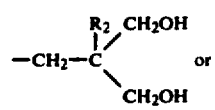

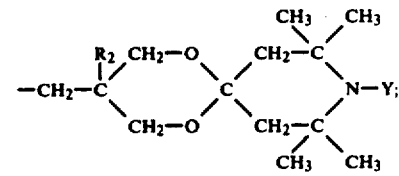

$R_2$ and $R_3$ may be taken together to form

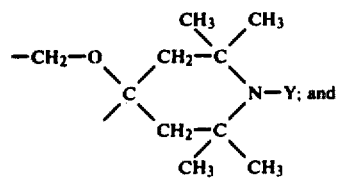

Y is selected from the group consisting of hydrogen and O·.

Minagawa et al, U.S. Pat. No. 4,128,608, patented Dec. 5, 1978, provides 2,2,6,6-tetramethyl-4-piperidyl spiro aliphatic ethers useful as stabilizers for organic polymeric materials, and having the general formula:

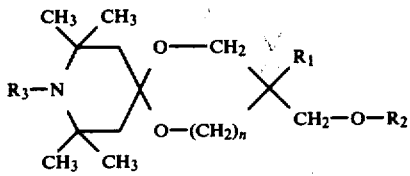

wherein:
$R_1$ is selected from the group consisting of hydrogen, lower alkyl and lower hydroxyalkyl having one or two carbon atoms;

$R_2$ is

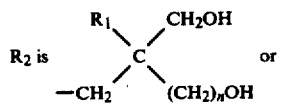

or

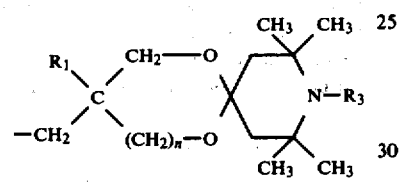

$R_3$ is selected from the group consisting of hydrogen and O-; and n is 0 to 1.

N-2-Hydroxyalkyl- or N-2,3-epoxypropyl-piperidine compounds are disclosed in Japan Kokai Nos. 65,180/73, 5,434/75, 5,435/75, 82,146/75, 111,140/75, Japanese patent No. 16,980/79 and Japanese patent No. 20,977/79.

The reaction products of glycidyl ethers or esters with piperidine compounds are disclosed in Japan Kokai No. 101,380/78. The reaction products of N-2,3-epoxypropyl piperidine compounds with dibasic acid anhydrides are shown in Japanese Kokai No. 66,996/79, and alkylene bispiperidine compounds are disclosed in Japan Kokai Nos. 32,937/74 and 35,239/75.

These compounds are, however, unsatisfactory in stabilizing effect, and applicable only for use as intermediates for the preparation of light stabilizers.

In accordance with the present invention, it has been discovered that N-2-hydroxy-3-substituted-piperidines of formula (I) below are superior in light stabilizing effectiveness to the corresponding N-2-hydroxyalkyl- or N-2,3-epoxy propylpiperidines.

The piperidine compounds of Formula (I) are characterized by at least one hydroxy group in a 2-hydroxypropyl group attached to the piperidyl nitrogen; the 2-hydroxy-propyl group either has a 3-hydroxy group in addition, or it has a 3-oxy group linking two piperidne rings. Many derivatives of these basic N-2-hydroxy-3-hydroxy or 3-oxy piperidine compounds of Formula (I) can be easily prepared, and are encompassed by the Formula. The compounds of this invention thus are useful also as intermediates for the preparation of even more effective light stabilizers.

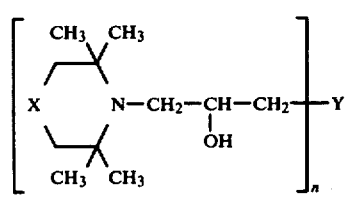

wherein X is selected from the group consisting of

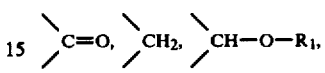

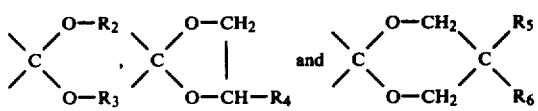

wherein
$R_1$ is selected from the group consisting of hydrogen; alkyl; alkenyl; cycloalkyl; alkaryl; hydroxyalkyl; oxyalkyl; acyl and aroyl having from one to about eighteen carbon atoms;

$R_2$ and $R_3$ are each selected from the group consisting of alkyl, alkenyl, cycloalkyl, alkaryl, hydroxyalkyl, oxyalkyl and haloalkyl having from one to about eighteen carbon atoms;

$R_4$, $R_5$ and $R_6$ each are selected from the group consisting of hydrogen, alkyl, alkenyl, cycloalkyl, alkaryl, hydroxyalkyl, oxyalkyl and haloalkyl having from one to about eighteen carbon atoms; and —$CH_2$—O—$R_1$;

n is 1 or 2; and

Y, when n is 1, is hydroxy or

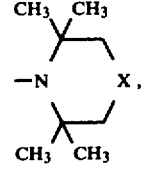

when n is 2, is oxyoxygen.

Exemplary $R_1$ acyl include formyl, acetyl, propionyl, butyroyl, hexanoyl, pivaroyl, octanoyl, decanoyl, lauroyl, myristoyl, palmitoyl, stearoyl, and 3,5-di-t-butyl-4-hydroxyphenyl propionyl; acryloyl, and methacryloyl.

Exemplary $R_1$ aroyl include benzoyl, toluoyl, p-t-butylbenzoyl, salicyloyl, and 3,5-di-t-butyl-4-hydroxybenzoyl.

Exemplary $R_1$, $R_2$, $R_3$, $R_4$, $R_5$ and $R_6$ alkyl include methyl, ethyl, propyl, isopropyl, butyl, sec-butyl, hexyl, octyl, isooctyl, 2-ethylhexyl, nonyl, decyl, dodecyl, tetradecyl, and octadecyl.

Exemplary alkenyl include allyl, butenyl, hexenyl, oleyl, linoleyl, and linolenyl.

Exemplary cycloalkyl include cyclopentyl, cyclohexyl, cycloheptyl and cyclooctyl.

Exemplary alkaryl include phenyl, phenylmethyl, and phenylethyl.

Exemplary hydroxyalkyl include 2-hydroxyethyl, 2-hydroxypropyl, and 2,3-dihydroxypropyl.

Exemplary oxyalkyl include 2,3-epoxypropyl and butoxyethyl.

Exemplary haloalkyl include chloromethyl and 2-hydroxy-3-chloromethyl.

The N-2-hydroxypropyl piperidines of this invention can be prepared in accordance with the process of the invention by reacting a piperidine compound of the structure:

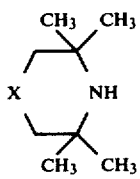

(wherein X is as in Formula (I)), with a 1,2-epoxy-3-substituted propane of the structure:

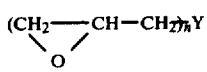

(wherein Y is as in Formula (I)) to add the desired 2-hydroxypropyl substituent to the piperidine compound. The reactants can be reacted directly or in the presence of a solvent.

Solvents which can be employed include water; aliphatic and cycloaliphatic alcohols such as methanol, ethanol, isopropanol, butanol, isobutanol, cyclohexanol, octanol and 2-ethylhexanol; aliphatic and cyclic ethers such as dioxane, tetrahydrofurane and diethylether; lower aliphatic ketones such as acetone and methyl ether ketone; aliphatic and aromatic hydrocarbons such as hexane, heptane, octane, benzene, toluene and xylene; and mixtures thereof.

The reaction can be carried out at from 10° C. to 200° C., preferably from 20° C. to 150° C.

The compounds of this invention also can be prepared by known methods, such as by hydrolyzing the corresponding 2,3-epoxypropyl piperidines or by reacting piperidine compounds with the corresponding 1-halo-2-hydroxy-3-substituted propanes. These procedures are, however, complicated, and the yields are low.

Therefore, the process of the present invention, preparing the N-2-hydroxy-3-substituted propyl piperidines from the corresponding 1,2-epoxy-3-substituted propanes, is to be preferred.

Exemplary compounds of Formula (I) are those below:

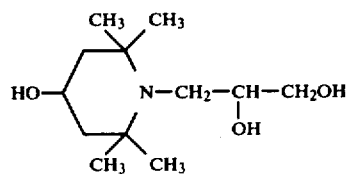
1.
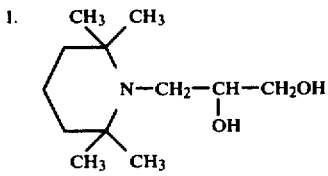
2.

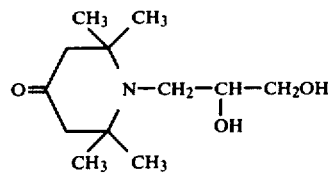
3.
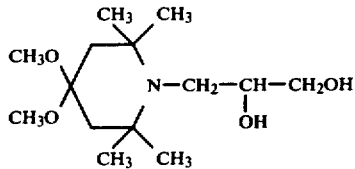
4.

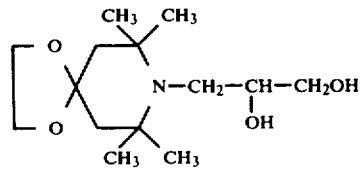
5.
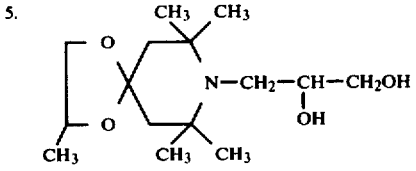
6.

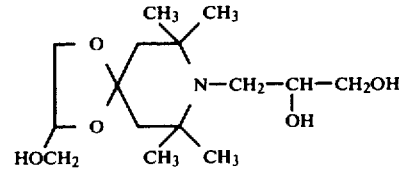
7.
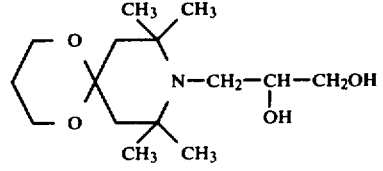
8.

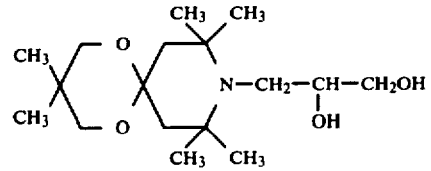
9.
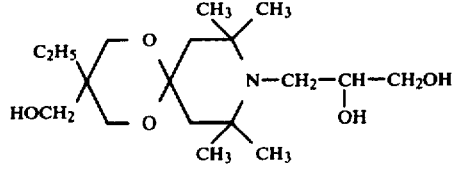
10.

-continued
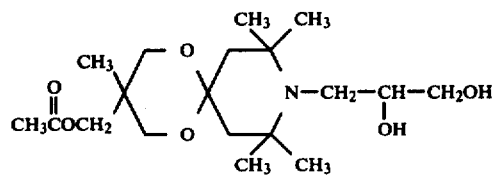 11.
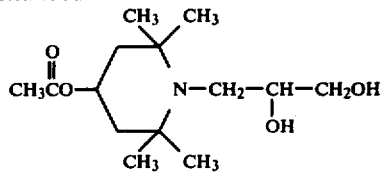 12.
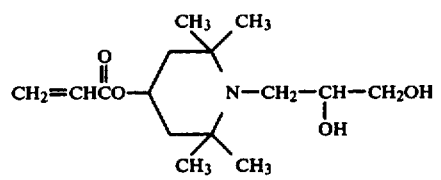 13.
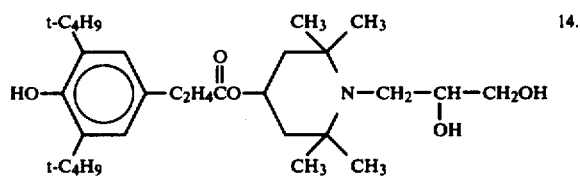 14.
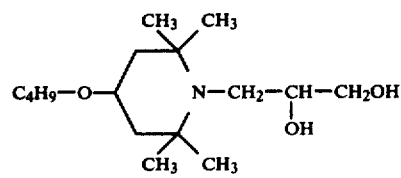 15.
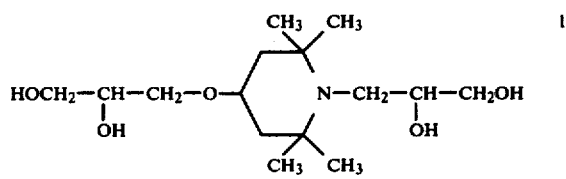 16.
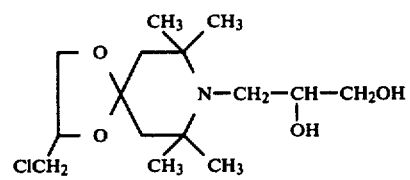 17.
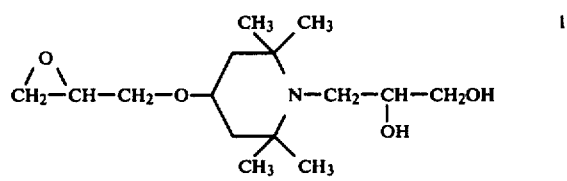 18.
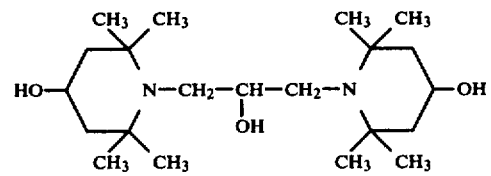 19.
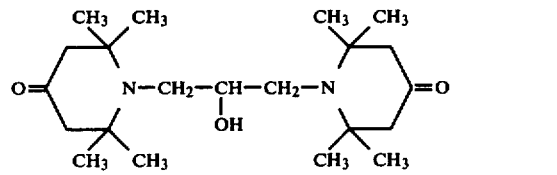 20.
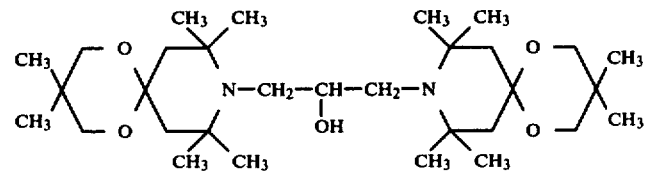 21.
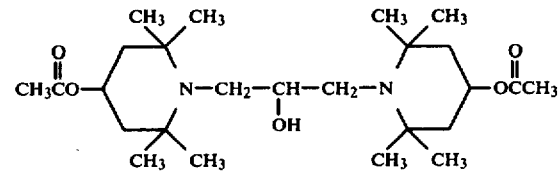 22.
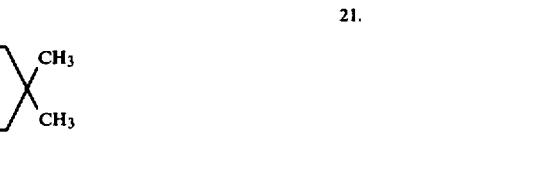
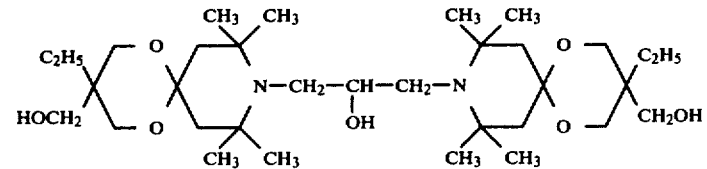 23.
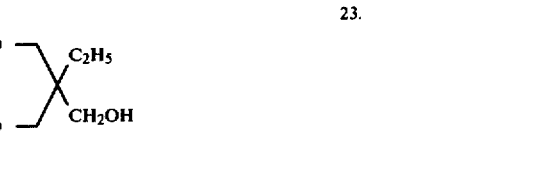
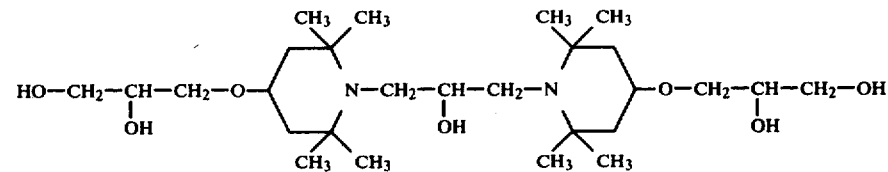 24.
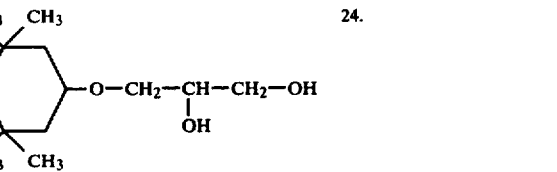

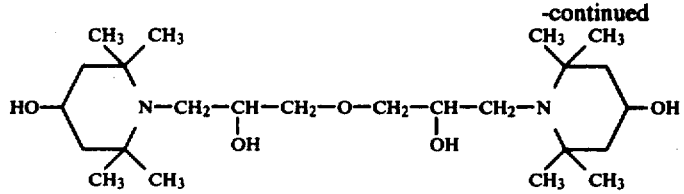 25.

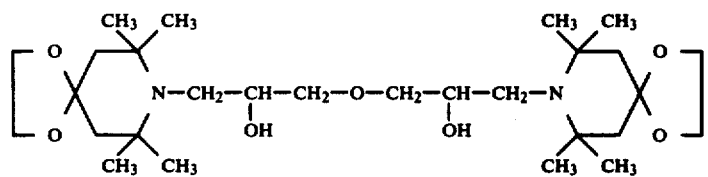 26.

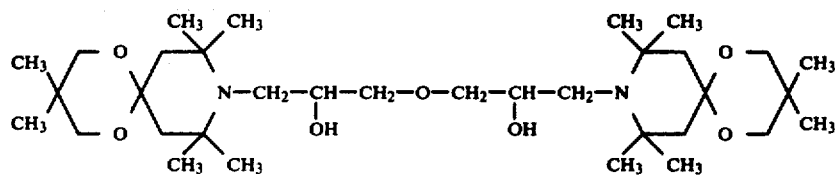 27.

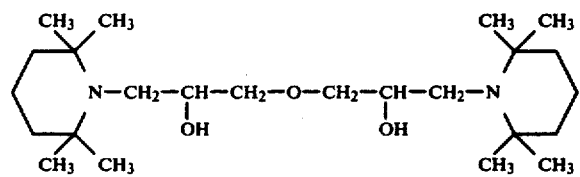 28.

The following Examples illustrate preferred embodiments of preparation of the compounds listed above, referring to the compounds by number:

EXAMPLE I

Preparation of N-(2′,3′-dihydroxypropyl)-2,2,6,6-tetramethyl-4-piperidinol (No. 1)

2,2,6,6-Tetramethyl-4-piperidinol 15.7 g and glycidol 7.8 g were dissolved in 50 ml of isopropanol and refluxed for five hours. Isopropanol was distilled off and the residue was recrystallized from n-hexane. A white powder, 21.3 g m.p. 97° to 99° C., was obtained.

Elemental analysis:

|  | C % | H % | N % |
|---|---|---|---|
| Calculated | 62.34 | 10.82 | 6.06 |
| Found | 62.47 | 10.88 | 6.01 |

Using the above procedure, the following compounds were prepared:

N-(2′,3′-Dihydroxypropyl)-2,2,6,6-tetramethyl piperidine(No. 2)

Colorless liquid.
Elemental analysis:

|  | C % | H % | N % |
|---|---|---|---|
| Calculated | 66.98 | 11.63 | 6.51 |
| Found | 67.12 | 11.60 | 6.58 |

N-(2′,3′-Dihydroxypropyl)2,2,6,6-tetramethyl piperidine-4-one (No. 3)

Pale yellow liquid.
Elemental analysis:

|  | C % | H % | N % |
|---|---|---|---|
| Calculated | 62.88 | 10.04 | 6.11 |
| Found | 62.75 | 10.10 | 6.15 |

N-(2′,3′-Dihydroxypropyl)-2,2,6,6-tetramethyl-4,4-dimethoxy piperidine (No. 4)

Pale yellow liquid.
Elemental analysis:

|  | C % | H % | N % |
|---|---|---|---|
| Calculated | 61.09 | 10.55 | 5.09 |
| Found | 61.15 | 10.48 | 5.13 |

N-(2′,3′-Dihydroxypropyl)-2,2,6,6-tetramethyl-4-acetoxy piperidine (No. 12)

Colorless liquid.
Elemental analysis:

|  | C % | H % | N % |
|---|---|---|---|
| Calculated | 61.54 | 9.89 | 5.13 |
| Found | 61.50 | 9.93 | 5.16 |

N-(2′,3′-Dihydroxypropyl)-2,2,6,6-tetramethyl-4-acryloyloxy piperidine (No. 13)

Pale yellow liquid.

Elemental analysis:

|  | C % | H % | N % |
| --- | --- | --- | --- |
| Calculated | 63.16 | 9.47 | 4.91 |
| Found | 63.21 | 9.40 | 4.86 |

N-(2',3'-Dihydroxypropyl)-2,2,6,6-tetramethyl-4-β-(3'',5''-di-t-butyl-4'''-hydroxyphenyl)propionyl oxypiperidine (No. 14)

Pale yellow sticky liquid.
Elemental analysis:

|  | C % | H % | N % |
| --- | --- | --- | --- |
| Calculated | 71.88 | 9.98 | 2.85 |
| Found | 71.93 | 9.96 | 2.87 |

N-(2',3'-Dihydroxypropyl)-2,2,6,6-tetramethyl-4-butoxy piperidine (No. 15)

Pale yellow liquid.
Elemental analysis:

|  | C % | H % | N % |
| --- | --- | --- | --- |
| Calculated | 66.90 | 11.50 | 4.88 |
| Found | 66.78 | 11.46 | 4.92 |

N-(2',3'-Dihydroxypropyl)-2,2,6,6-tetramethyl-4-(2',3'-dihydroxypropoxy) piperidine (No. 16)

Colorless sticky liquid.
Elemental analysis:

|  | C % | H % | N % |
| --- | --- | --- | --- |
| Calculated | 59.02 | 10.16 | 4.59 |
| Found | 59.15 | 10.13 | 4.64 |

N-(2',3'-Dihydroxypropyl)-2,2,6,6-tetramethyl-4-(2'',3''-epoxypropoxy) piperidine (No. 18)

Colorless liquid.
Elemental analysis:

|  | C % | H % | N % |
| --- | --- | --- | --- |
| Calculated | 62.72 | 10.10 | 4.88 |
| Found | 62.66 | 10.07 | 4.90 |

EXAMPLE II

Preparation of N-(2',3'-dihydroxypropyl)-9-aza-3,3,8,8,10,10-hexamethyl-1,5-dioxaspiro(5,5)undecane (No. 9)

9-Aza-3,3,8,8,10,10-hexamethyl-1,5-dioxaspiro(5,5)undecane 24.1 g was dissolved in water/ethanol (1:2) mixed solvent and glycidol 7.8 g was added. After refluxing for eight hours, solvent and unreacted raw materials were distilled off under reduced pressure, and 27.1 g of pale yellow liquid was obtained.
Elemental analysis:

|  | C % | H % | N % |
| --- | --- | --- | --- |
| Calculated | 64.76 | 10.48 | 4.44 |
| Found | 64.88 | 10.45 | 4.50 |

Using the above procedure, the following compounds were prepared:

N-(2',3'-Dihydroxypropyl)-8-aza-7,7,9,9-tetramethyl-1,4-dioxaspiro(4,5)decane (No. 5)

Colorless liquid.
Elemental analysis:

|  | C % | H % | N % |
| --- | --- | --- | --- |
| Calculated | 61.54 | 9.89 | 5.13 |
| Found | 61.35 | 9.82 | 5.18 |

N-(2',3'-Dihydroxypropyl)-8-aza,2,7,7,9,9-pentamethyl-1,4-dioxaspiro(4,5)decane (No. 6)

Pale yellow liquid.
Elemental analysis:

|  | C % | H % | N % |
| --- | --- | --- | --- |
| Calculated | 62.72 | 10.10 | 4.88 |
| Found | 62.90 | 10.02 | 4.91 |

N-(2',3'-Dihydroxypropyl)-8-aza-2-hydroxymethyl-7,7,9,9-tetramethyl-1,4-dioxaspiro(4,5)decane (No. 7)

|  | C % | H % | N % |
| --- | --- | --- | --- |
| Calculated | 59.41 | 9.57 | 4.62 |
| Found | 59.54 | 9.52 | 4.57 |

N-(2',3'-Dihydroxypropyl)-9-aza-8,8,10,10-tetramethyl-1,5-dioxaspiro(5,5)undecane (No. 8)

Colorless liquid.
Elemental analysis:

|  | C % | H % | N % |
| --- | --- | --- | --- |
| Calculated | 62.72 | 10.10 | 4.88 |
| Found | 62.83 | 10.05 | 4.81 |

N-(2,3-Dihydroxypropyl)-9-aza-3-ethyl-3-hydroxymethyl-8,8,10,10-tetramethyl-1,5-dioxaspiro(5,5)undecane (No. 10)

White powder m.p. 52° to 55° C.
Elemental analysis:

|  | C % | H % | N % |
| --- | --- | --- | --- |
| Calculated | 62.61 | 10.14 | 4.06 |
| Found | 62.55 | 10.17 | 4.08 |

N-(2',3'-Dihydroxypropyl)-9-aza-3-acetoxymethyl-3,8,8,10,10-pentamethyl-1,5-dioxaspiro(5,5)undecane (No. 11)

Pale yellow sticky liquid.
Elemental analysis:

|  | C % | H % | N % |
|---|---|---|---|
| Calculated | 61.13 | 9.38 | 3.75 |
| Found | 61.25 | 9.35 | 3.81 |

N-(2,3-Dihydroxypropyl)-2-chloromethyl-8-aza-7,7,9,9-tetramethyl-1,4-dioxaspiro(4,5)decane (No. 17)

Pale yellow liquid.
Elemental analysis:

|  | C % | H % | N % |
|---|---|---|---|
| Calculated | 55.99 | 8.71 | 4.35 |
| Found | 56.12 | 8.67 | 4.31 |

EXAMPLE III

Preparation of 1,3-bis(2,2,6,6-tetramethyl-4-hydroxy piperidine-1-yl)-2-hydroxypropane (No. 19)

N-(2',3'-Epoxypropyl)-2,2,6,6-tetramethyl-4-hydroxy piperidine 21.3 g and 2,2,6,6-tetramethyl-4-hydroxy piperidine 15.7 g were dissolved in 50 ml toluene, and 0.5 g phenol was added. After refluxing for eight hours, the solvent was distilled off, and the residue was recrystallized from toluene. A white powder, 22.7 g, m.p. 186° to 190° C., was obtained.
Elemental analysis:

|  | C % | H % | N % |
|---|---|---|---|
| Calculated | 68.11 | 11.35 | 7.57 |
| Found | 68.24 | 11.33 | 7.50 |

Using the above procedure, the following compounds were prepared:

1,3-Bis(2,2,6,6-tetramethyl-4-oxopiperidine-1-yl)-2-hydroxy propane (No. 20)

White powder m.p. 116° to 122° C.
Elemental analysis:

|  | C % | H % | N % |
|---|---|---|---|
| Calculated | 68.85 | 10.38 | 7.65 |
| Found | 68.76 | 10.41 | 7.63 |

N,N'-(2-Hydroxytrimethylene)bis(9-aza-3,3,8,8,10,10-hexamethyl-1,5-dioxaspiro(5,5)undecane) (No. 21)

White powder m.p. 133° to 138° C.
Elemental analysis:

|  | C % | H % | N % |
|---|---|---|---|
| Calculated | 69.14 | 10.78 | 5.20 |
| Found | 69.20 | 10.73 | 5.16 |

1,3-Bis(2,2,6,6-tetramethyl-4-acetoxy piperidine-1-yl)-2-hydroxypropane (No. 22)

Colorless liquid.
Elemental analysis:

|  | C % | H % | N % |
|---|---|---|---|
| Calculated | 66.08 | 10.13 | 6.17 |
| Found | 65.97 | 10.15 | 6.14 |

N,N'-(2-Hydroxytrimethylene)bis(9-aza-8,8,10,10-tetramethyl-3-ethyl-3-hydroxymethyl-1,5-dioxaspiro(5,5)undecane) (No. 23)

White powder m.p. 136° to 141° C.
Elemental analysis:

|  | C % | H % | N % |
|---|---|---|---|
| Calculated | 66.22 | 10.37 | 4.68 |
| Found | 66.30 | 10.34 | 4.63 |

1,3-Bis(2,2,6,6-tetramethyl-4-(2',3'-dihydroxypropoxy) piperidine-1-yl)-2-hydroxypropane (No. 24)

Pale yellow liquid.
Elemental analysis:

|  | C% | H% | N% |
|---|---|---|---|
| Calculated | 62.55 | 10.42 | 5.41 |
| Found | 62.48 | 10.39 | 5.46 |

EXAMPLE IV

Preparation of bis(2-hydroxy-3-(2,2,6,6-tetramethyl-4-hydroxypiperidine-1-yl)propyl)ether (No. 25)

2,2,6,6-Tetramethyl-4-hydroxypiperidine 15.7 g and bis(2,3-epoxypropyl)ether was dissolved in 30 ml ethanol and refluxed for ten hours. Ethanol was distilled off, and 21.8 g of colorless liquid was obtained.
Elemental analysis:

|  | C% | H% | N% |
|---|---|---|---|
| Calculated | 64.86 | 10.81 | 6.31 |
| Found | 64.88 | 10.84 | 6.37 |

Using the above procedure, the following compounds were prepared:

Bis(2-hydroxy-3-(8-aza-7,7,9,9-tetramethyl-1,4-dioxaspiro(4,5)decane-8-yl)propyl)ether (No. 26)

Pale yellow liquid.
Elemental analysis:

|  | C% | H% | N% |
|---|---|---|---|
| Calculated | 63.64 | 9.85 | 5.30 |
| Found | 63.67 | 9.82 | 5.36 |

Bis(2-hydroxy-3-(9-aza-3,3,8,8,10,10-hexamethyl-1,5-dioxaspiro(5,5)undecane-9-yl)propyl)ether (No. 27)

Pale yellow liquid.
Elemental analysis:

|  | C% | H% | N% |
|---|---|---|---|
| Calculated | 66.67 | 10.46 | 4.58 |

|  | C% | H% | N% |
|---|---|---|---|
| Found | 66.62 | 10.42 | 4.61 |

Bis(2-hydroxy-3-(2,2,6,6-tetramethyl piperidine-1-yl)-propyl)ether (No. 28)

Colorless liquid.
Elemental analysis:

|  | C% | H% | N% |
|---|---|---|---|
| Calculated | 69.90 | 11.65 | 6.80 |
| Found | 69.82 | 11.62 | 6.85 |

The N-2-hydroxypropyl-3-substituted piperidines of the invention can be combined with conventional heat stabilizers such as phenolic antioxidant heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

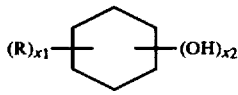

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

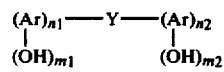

wherein Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar-Y-Ar-Y-Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

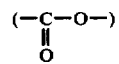

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

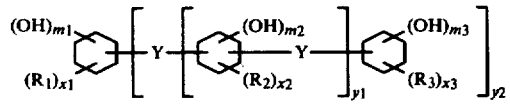

wherein
$R_1$, $R_2$ and $R_3$ are inert substituent groups as described in the previous paragraph;
$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

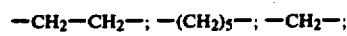

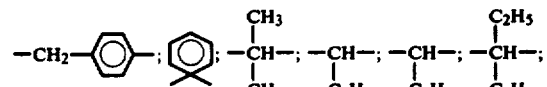

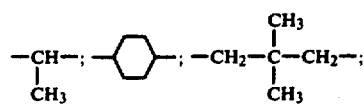

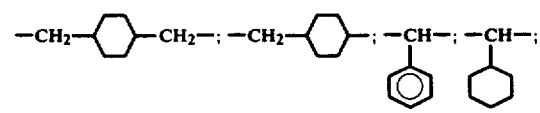

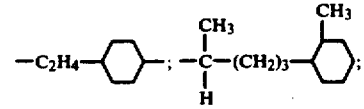

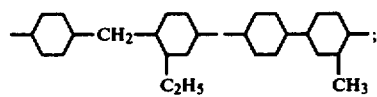

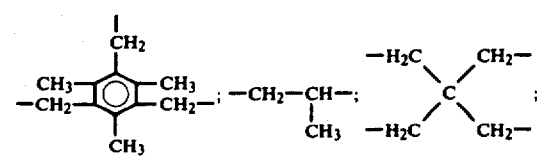

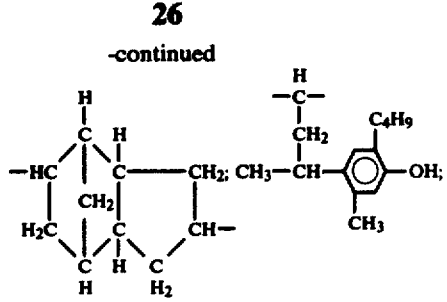

(2) Y groups where only atoms other than carbon link the aromatic rings, such as —O—, —S—,

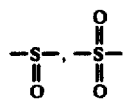

and —(S)$_x$— where x is a number from one to ten;

(3) Y groups made up of more than a single atom including both carbon and other atoms linking the aromatic nuclei, such as:

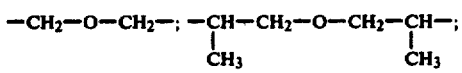

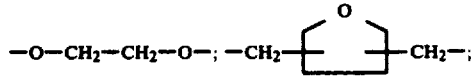

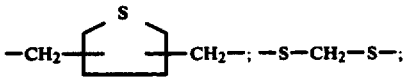

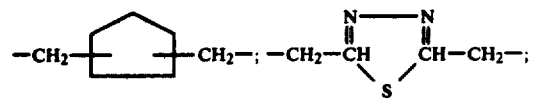

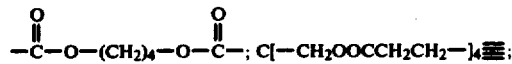

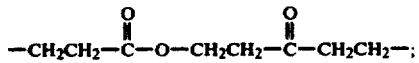

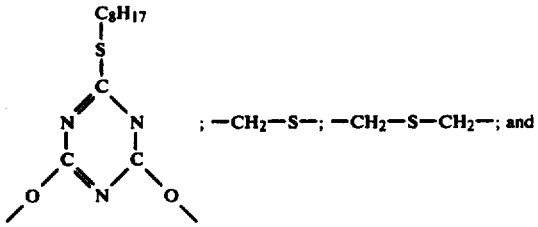

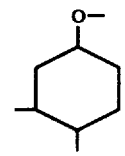

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenylphenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxyphenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl (4-hydroxy-3-methyl-5-t-butyl)benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexylcatechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis(2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methyl-phenol), 2,2'-methylene-bis-(4-methyl-6-(1'-methyl-cyclohexyl)-phenol), 4,4'-cyclohexylene bis-(2-tertiary-butyl-phenol), 2,6-bis-(2'-hydroxy-3'-t-butyl-5'-methyl-benzyl)-4-methyl-phenol, 4,4'-oxobis(naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl)propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxy-phenyl)-(3',5'-di-tert-butyl-4',4-hydroxyphenyl)ethane, 2,2'-methylene-bis-(4-octylphenol), 4,4'-propylene-bis-(2-tert-butyl-phenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylbutylene-4,4'-bisphenol, 4,4'-cyclooctylene-bis-(2-cyclohexylphenol),β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl)sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methyl-benzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid]glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis[methylene-3(3,5-di-t-butyl-4-hydroxyphenyl)propionate]methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and penta-erythritol hydroxyphenyl propionate.

A particularly desirable class of polyhydric polyclic phenols are the dicyclopentadiene polyphenols, which are of the type:

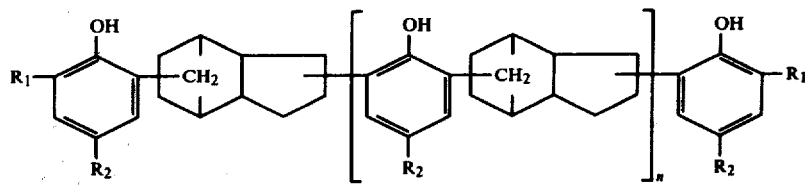

in which
R₁ and R₂ are lower alkyl, and can be the same or different, and
n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

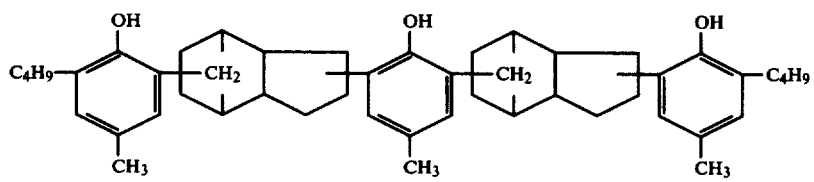

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

In addition, the stabilizer compositions of the invention can include other stabilizers conventionally used as heat and/or light stabilizers for synthetic resins, including polyvalent metal salts of organic acids, organic triphosphites and acid phosphites.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophisphites.

The organic triphosphites in which the radicals are monovalent radicals can be defined by the formula:

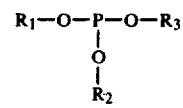

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

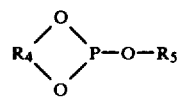

in which
  $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$;
  $R_5$ is hydrogen or a cation, in the case of the acid phosphites.

Also useful organic triphosphites are mixed heterocyclic-open chain phosphites of the type:

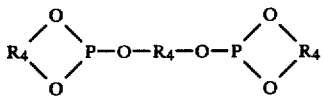

More complex triphosphites are formed from trivalent organic radicals, of the type:

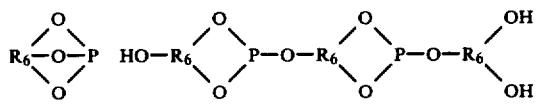

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

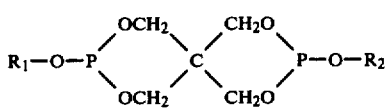

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

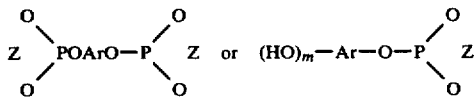

in which Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$-Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl)phosphite, tri-(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-cyclohexylphenyl)phosphite), tri-α-naphthyl phosphite, tri(-phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane(diphenyl-pentaerythritol diphosphite), 3,9-di(decyloxy)-2,4,8,10-tetraoxa-3,9-diphosphaspiro(5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy)ethyloxy group has an average molecular weight of 350), 3,9-di(methoxy(polyethoxy)ethyloxy)-2,4,8,10-tetraoxa-3,9-diphosphaspiro-(5,5)-undecane (where the (polyethoxy)ethyloxy group has an average molecular weight of 550).

Exemplary of the bis aryl triphosphites are: bis(4,4'-thio-bis(2-tertiary-butyl-5-methyl-phenol))isooctyl phosphite, mono(4,4'-thio-bis(2-tertiary-butyl-5-methylphenol))di-phenyl phosphite, tri-(4,4'-n-butylidene-bis(2-tertiary-butyl-5-methylphenol))phosphite, (4,4'-benzylidene-bis(2-tertiary-butyl-5-methyl-phenol)-)diphenyl phosphite, isooctyl 2,2'-bis(-parahydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl(2,6-bis(2'-hydroxy-3,5-dinonylbenzyl)-4-nonyl phenyl))phosphite, tetra-tridecyl-4,4'-n-butylidene-bis(2-tertiary-butyl-5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bisphenyl polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiary-butyl-5-methylphenyl)diphosphite, tetra-tridecyl-4,4'-isopropylidene bisphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, dicresyl phosphite, di-(o-isooctylphenyl)phosphite, di(p-ethylhexylphenyl)phosphite, di(p-t-octylphenyl)phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol))-phosphite, (4,4'-thio-bis(2-tertiary-butyl-5-methylphenol))phenyl phosphite, bis(4,4'-n-butylidene-bis(2-tertiary-butyl-5-methylphenol))phosphite, mono(4,4'-benzylidene-bis(2-tertiary-butyl-5-methylphenol))-phosphite, mono(2,2'-bis-(parahydroxyphenyl)-propane)phosphite, mono(4,4'-butylidene-bis(2-tertiary-butyl-5-methylphenol)phosphite, bis(4,4'-thio-bis(2-tertiary-butyl-5-methylphenyl))phosphite, mono-2-ethylhexyl-mono-2,2'-methylene-bis(4-methyl-6,1'-methyl-cyclohexyl)phenol phosphite, bis(2,2'-bis(para-hydroxyphenyl)propane)phosphite, monoisooctylmono(4,4'-thio-bis(2-tertiary-butyl-5-methylphenol))phosphite, isooctyl-(2,6-bis(2'-hydroxy-3,5-dinonylbenzyl)-4-nonylphenyl))phosphite, tri-tridecyl-4,4'-n-butylidene-bis(2-tertiary-butyl-5-methylphenyl)diphosphite, trii-sooctyl-4,4'-thio-bis(2-tertiary-butyl-5-methylphenyl)-diphosphite, bis(2,2'-methylene-bis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene-bis(2-tertiary-butyl-5-methylphenyl)diphosphite, di-tridecyl-4,4'-isopropylidene bisphenyl diphosphite, tetra-tridecyl butane-1,1,3-tris(2'-methyl-5-tertiary-butylphenyl-4)-triphosphite.

Other conventional additives that can be employed with the N-2-hydroxypropyl pyridines of this invention include thioether antioxidants, UV absorbers, metal deactivators, chelating agents, organotin compounds, plasticizers, epoxy compounds, pigments, fillers, foaming agents, antistatic agents, flame-retardants, lubricants and processing aids.

The N-2-hydroxypropyl-3-substituted-piperidine stabilizers, especially in combination with phenolic antioxidants, and, optionally, other stabilizers, in the stabilizer compositions of the invention, are effective stabilizers to enhance the resistance to deterioration due to heat of synthetic polymeric materials which are susceptible to such degradation.

The stabilizer systems of the invention are especially effective heat stabilizers for olefin polymers such as polyethylene, polypropylene, polybutylene, polypentylene, polyisopentylene, and higher polyolefins.

Olefin polymers on exposure to elevated temperatures undergo degradation, resulting in embrittlement and discoloration.

The stabilizer systems can be employed with any olefin polymer, including low-density polyethylene, high density polyethylene, polyethylenes prepared by the Ziegler-Natta process, polypropylenes prepared by the Ziegler-Natta process, and by other polymerization methods from propylene, poly(butene-1)poly(pentene-1)poly(3-methylbutene-1)poly(4-methylpentene-1), polystyrene, and mixtures of polyethylene and polypropylene with other compatible polymers, such as mixtures of polyethylene and polypropylene, and copolymers of such olefins, such as copolymers of ethylene, propylene, and butene, with each other and with other copolymerizable monomers, such as ethylene-vinyl acetate copolymer, which present the instability problem that is resolved by the stabilizer system of the invention. The term "olefin polymer" encompasses both homopolymers and copolymers.

Polypropylene solid polymer can be defined in a manner to differentiate it from other polyolefins as having a density within the range from 0.86 to 0.91, and a melting point above 150° C. The stabilizer system of the invention is applicable to all such polypropylenes, as distinguished from polypropylenes in the liquid form or im semiliquid or gel-like forms, such as are used as greases and waxes.

The stabilizers of the invention are applicable to polypropylenes prepared by any of the various procedures, for the molecular weight and tacticity are not factors affecting this stabilizer system. Isotactic polypropylene, available commercially under the trade name PROFAX, and having a softening or hot-working temperature of about 350° F., is an example of a sterically regular polypropylene polymer.

Mixtures of polypropylene with other compatible polymers and copolymers of propylene with copolymerizable monomers not reactive with the polypropylene stabilizer combination can also be stabilized, for example, mixtures of polyethylene and polypropylene, and copolymers of propylene and ethylene which have a sufficient amount of propylene to present the instability problem that is resolved by the stabilizer combinations of the invention.

The stabilizers are also effective to enhance the resistance to heat degradation of polystyrene; polydienes, such as polybutadiene and polyisoprene; and copolymers of olefins and dienes with other ethylenically and acetylenically unsaturated monomers, such as ethylene-vinyl acetate copolymers, copolymers from styrene and another monomer (for example, maleic anhydride, butadiene, acrylonitrile, and so on); styrene-butadiene copolymers, acrylonitrile-styrene-butadiene copolymers, synthetic rubbers of all types, such as polychloroprene, polyacrylic ester resins, acrylic acid ester-butadiene-styrene copolymer, methacrylic acid ester-butadiene-styrene copolymer, methacrylate ester resin such as polymethacrylate; polyvinyl acetate; polyvinyl halides, including polyvinyl chloride homopolymer, polyvinylidene chloride; and copolymers of vinyl chloride and vinylidene chloride; vinyl chloride and vinyl acetate; vinylidene chloride and vinyl acetate; polyvinylidene fluoride and copolymers thereof; and other ethylenically unsaturated monomers; polyvinylalcohol, polyvinylformal, polyvinylbutyral; polyacetals such as polyoxymethylene and polyoxyethylene; polyesters such as polyethylene glycol-terephthalic acid ester polymers;

polyamides such as polyepsilon-caprolactam; polyhexamethylene adipamide, and polydecamethylene adipamide; polyurethanes; polycarbonates; and epoxy resins; and rubbers such as isoprene rubber, butadiene rubber, epichlorohydrin rubber, chloroprene rubber, and blends of the above resins, fat, oil, mineral oil, soap, cream, natural and synthetic wax and ester oil; cellulose esters such as cellulose acetate, cellulose propionate, cellulose butyrate, and cellulose acetate-propionate; phenol-formaldehyde resins, urea-formaldehyde resins, melamine-formaldehyde resins, unsaturated polyester resins, and silicone resins.

The synthetic polymer can be in any physical form, including (for example) filaments, yarns, films, sheets, molded articles, latex, and foam.

A sufficient amount of the stabilizer or combination is used to improve the resistance of the synthetic polymer to deterioration in physical properties, including, for example, discoloration, reduction in melt viscosity and embrittlement, under the conditions to which the polymer will be subjected. Very small amounts are usually adequate. Amounts within the range from about 0.001 to about 10% total stabilizers including the N-2-hydroxypropyl pyridine by weight of the polymer are satisfactory. Preferably, from 0.01 to 3% including the N-2-hydroxypropyl pyridine is employed for optimum stabilization.

Inasmuch as all components are solids, the stabilizer systems of the invention are readily rendered in solid particulate form, comprising a blend of:

(a) N-2-hydroxypropyl pyridine in an amount of from about 10 to about 35 parts by weight; and optionally:

(b) a phenolic antioxidant in an amount from about 10 to about 35 parts by weight; and/or (c) other heat or light stabilizers in an amount of from about 10 to about 35 parts by weight.

The N-2-hydroxypropyl pyridines of the invention can be employed as the sole stabilizer or in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

Preferably, the stabilizer system is added to the synthetic polymer in an amount to provide in the polymer from about 0.001 to about 10% of the N-2-hydroxypropyl pyridine, and optionally, from about 0.001 to about 5% of phenolic antioxidant and/or other heat or light stabilizer.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples represent preferred embodiments of synthetic resin compositions having their resistance to deterioration enhanced by the piperidyl compounds of the invention:

EXAMPLES 1 to 16

Polypropylene compositions were prepared using stabilizers of the invention and five of the prior art, and having the following formulation:

| Ingredient | Parts by Weight |
|---|---|
| Polypropylene | 100 |
| Stearyl-(3,5-di-t-butyl-4-hydroxyphenyl) propionate | 0.2 |
| Stabilizer as shown in Table I | 0.3 |

The compositions were thoroughly blended and then compression-molded to form sheets 0.3 mm thick. Pieces 2.5 cm × 5 cm were cut off from the sheets and exposed to a high voltage mercury lamp until failure, evidenced by discoloration and/or embrittlement. The hours to failure were noted, and the results are shown in Table I.

TABLE I

| Control | Stabilizer | Hours to failure |
|---|---|---|
| 1 | N—(2'-Hydroxyethyl)-2,2,6,6-tetramethyl-4-piperidinol | 150 |
| 2 | N—(2',3'-Epoxypropyl)-8-aza-7,7,9,9-tetramethyl-1,4-dioxaspiro (4,5) decane | 180 |
| 3 | N—(2'-Hydroxyethyl)-9-aza-3,3,8,8,10,10-hexamethyl-1,5-dioxaspiro (5,5) undecane | 160 |
| 4 | N—(2',3'-Epoxypropyl)-9-aza-3-ethyl-3-hydroxymethyl-8,8,10,10- | 210 |

TABLE I-continued

| | | Hours to failure |
|---|---|---|
| 5 | tetramethyl-1,5-dioxaspiro (5,5) undecane | |
| 5 | N,N'—Hexamethylenebis(8-aza-7,7,9,9-tetramethyl-1,4-dioxaspiro (4,5) decane) | 290 |

| Example No. | Piperidyl Compound | Hours to failure |
|---|---|---|
| 1 | HO–[2,2,6,6-tetramethylpiperidine]–N–CH$_2$–CH(OH)–CH$_2$OH | 550 |
| 2 | (CH$_3$O)$_2$–[2,2,6,6-tetramethylpiperidine]–N–CH$_2$–CH(OH)–CH$_2$OH | 470 |
| 3 | spiro-dioxolane–[2,2,6,6-tetramethylpiperidine]–N–CH$_2$–CH(OH)–CH$_2$OH | 490 |
| 4 | HOCH$_2$-substituted spiro-dioxane–[2,2,6,6-tetramethylpiperidine]–N–CH$_2$–CH(OH)–CH$_2$OH | 520 |
| 5 | (CH$_3$)$_2$-substituted spiro-dioxane–[2,2,6,6-tetramethylpiperidine]–N–CH$_2$–CH(OH)–CH$_2$OH | 540 |
| 6 | C$_2$H$_5$, HOCH$_2$-substituted spiro-dioxane–[2,2,6,6-tetramethylpiperidine]–N–CH$_2$–CH(OH)–CH$_2$OH | 500 |
| 7 | CH$_3$C(O)O–[2,2,6,6-tetramethylpiperidine]–N–CH$_2$–CH(OH)–CH$_2$OH | 520 |
| 8 | 3,5-di-t-C$_4$H$_9$-4-HO–C$_6$H$_2$–C$_2$H$_4$C(O)O–[2,2,6,6-tetramethylpiperidine]–N–CH$_2$–CH(OH)–CH$_2$OH | 490 |

TABLE I-continued

| # | Structure | Value |
|---|---|---|
| 9 | HOCH₂—CH(OH)—CH₂—O—[2,2,6,6-tetramethylpiperidin-4-yl with N—CH₂—CH(OH)—CH₂OH] | 510 |
| 10 | CH₂(epoxide)—CH—CH₂—O—[2,2,6,6-tetramethylpiperidin-4-yl with N—CH₂—CH(OH)—CH₂OH] | 500 |
| 11 | HO—[2,2,6,6-tetramethylpiperidin-4-yl]—N—CH₂—CH(OH)—CH₂—N—[2,2,6,6-tetramethylpiperidin-4-yl]—OH | 560 |
| 12 | (CH₃)₂C(CH₂—O—)₂ ketal on 2,2,6,6-tetramethylpiperidin-4-one—N—CH₂—CH(OH)—CH₂—N—[same ketal-piperidinyl]—C(CH₃)₂ | 540 |
| 13 | C₂H₅(HOCH₂)C(CH₂—O—)₂ ketal on 2,2,6,6-tetramethylpiperidin-4-one—N—CH₂—CH(OH)—CH₂—N—[same]—C(C₂H₅)(CH₂OH) | 540 |
| 14 | HO—[2,2,6,6-tetramethylpiperidin-4-yl]—N—CH₂—CH(OH)—CH₂—O—CH₂—CH(OH)—CH₂—N—[2,2,6,6-tetramethylpiperidin-4-yl]—OH | 520 |
| 15 | [—O—C(CH₂O)₂— spiroketal on 2,2,6,6-tetramethylpiperidin-4-yl—N—CH₂—CH(OH)—CH₂—O—CH₂—CH(OH)—CH₂—N—piperidinyl-spiroketal—] | 500 |
| 16 | (CH₃)₂C(CH₂—O—)₂ ketal on 2,2,6,6-tetramethylpiperidin-4-yl—N—CH₂—CH(OH)—CH₂—O—CH₂—CH(OH)—CH₂—N—[same]—C(CH₃)₂ | 530 |

The improvement in resistance to degradation in ultraviolet light that is imparted by the stabilizers of the invention, as compared to the prior art, is apparent from the above results.

EXAMPLES 17 to 26

High density polyethylene compositions were prepared using the stabilizers of the invention and five of the prior art, and having the following formulation:

| Ingredient | Parts by Weight |
|---|---|
| High-density polyethylene | 100 |
| Ca stearate | 1 |
| Tetrakis-(methylene-3-(3,5-di-t-butyl-4-hydroxyphenyl)propionate) methane | 0.1 |
| Distearyl thiodipropionate | 0.3 |
| Stabilizer as shown in Table II | 0.2 |

The stabilizer was blended with the polymer on a two-roll mill, and sheets 0.5 mm thick were prepared by compression molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table II.

TABLE II

| Control | Stabilizer | Hours to failure |
|---|---|---|
| 6 | N—(2'-Hydroxyethyl)-2,2,6,6-tetramethyl-4-piperidinol | 440 |
| 7 | N—(2',3'-Epoxypropyl)-8-aza-7,7,9,9-tetramethyl-1,4-dioxaspiro (4,5) decane | 510 |
| 8 | N—(2'-Hydroxyethyl)-9-aza-3,3,8,8,10,10-hexamethyl-1,5-dioxaspiro (5,5) undecane | 470 |
| 9 | N—(2',3'-Epoxypropyl)-9-aza-3-ethyl-3-hydroxymethyl-8,8,10,10-tetramethyl-1,5-dioxaspiro (5,5) undecane | 490 |
| 10 | N,N'-hexamethylenebis (8-aza-7,7,9,9-tetramethyl-1,4-dioxaspiro (4,5) decane) | 570 |

| Example No. | Stabilizer | Hours to failure |
|---|---|---|
| 17 | [structure] | 890 |
| 18 | [structure] | 830 |
| 19 | [structure] | 850 |
| 20 | [structure] | 830 |
| 21 | [structure] | 800 |

TABLE II-continued

| | | |
|---|---|---|
| 22 | HOCH$_2$—CH(OH)—CH$_2$—O—[piperidine(CH$_3$)$_4$]—N—CH$_2$—CH(OH)—CH$_2$OH | 860 |
| 23 | HO—[piperidine(CH$_3$)$_4$]—N—CH$_2$—CH(OH)—CH$_2$—N—[piperidine(CH$_3$)$_4$]—OH | 970 |
| 24 | (CH$_3$)$_2$C(O—)$_2$—[piperidine(CH$_3$)$_4$]—N—CH$_2$—CH(OH)—CH$_2$—N—[piperidine(CH$_3$)$_4$]—(O—)$_2$C(CH$_3$)$_2$ | 920 |
| 25 | HO—[piperidine(CH$_3$)$_4$]—N—CH$_2$—CH(OH)—CH$_2$—O—CH$_2$—CH(OH)—CH$_2$—N—[piperidine(CH$_3$)$_4$]—OH | 920 |
| 26 | (CH$_3$)$_2$C(O—)$_2$—[piperidine(CH$_3$)$_4$]—N—CH$_2$—CH(OH)—CH$_2$—O—CH$_2$—CH(OH)—CH$_2$—N—[piperidine(CH$_3$)$_4$]—(O—)$_2$C(CH$_3$)$_2$ | 880 |

The improvement in resistance to degradation in ultraviolet light that is imparted by the stabilizers of the invention, as compared to the prior art, is apparent from the above results.

Having regard to the foregoing disclosure, the following is claimed as inventive and patentable embodiments thereof:

1. An N-2-hydroxypropyl piperidine having the formula:

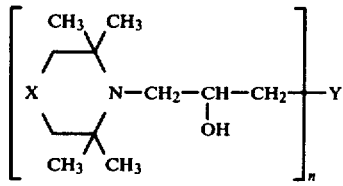

(I)

wherein

X is selected from the group consisting of

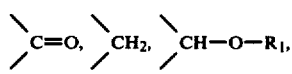

-continued $$\begin{array}{c} \diagdown \\ C \\ \diagup \end{array} \begin{array}{c} O-R_2 \\ \\ O-R_3 \end{array}, \begin{array}{c} \diagdown \\ C \\ \diagup \end{array} \begin{array}{c} O-CH_2 \\ | \\ O-CH-R_4 \end{array} \text{ and } \begin{array}{c} \diagdown \\ C \\ \diagup \end{array} \begin{array}{c} O-CH_2 \\ \\ O-CH_2 \end{array} \begin{array}{c} \diagup \\ C \\ \diagdown \end{array} \begin{array}{c} R_5 \\ \\ R_6 \end{array}$$

wherein

R$_1$ is selected from the group consisting of hydrogen; alkyl; alkenyl; cycloalkyl; alkaryl; hydroxyalkyl; oxyalkyl; carboxylic acyl; and aroyl, all of the preceding having from one to about eighteen carbon atoms;

R$_2$ and R$_3$ are each selected from the group consisting of alkyl, alkenyl, cycloalkyl, alkaryl, hydroxyalkyl, oxyalkyl and haloalkyl having from one to about eighteen carbon atoms;

R$_4$, R$_5$ and R$_6$ each are selected from the group consisting of hydrogen, alkyl, alkenyl, cycloalkyl, alkaryl, hydroxyalkyl, oxyalkyl and haloalkyl having from one to about eighteen carbon atoms; and —CH$_2$—O—R$_1$;

n is 1 or 2; and

Y, when n is 1, is hydroxy or

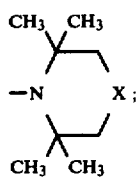

and when n is 2, is oxy—O—.

2. An N-2-hydroxypropyl piperidine according to claim 1 in which X is >CH$_2$OH, n is 1 and Y is H.

3. An N-2-hydroxypropyl piperidine according to claim 1 in which X is >CH$_2$, n is 1, and Y is H.

4. An N-2-hydroxypropyl piperidine according to claim 3 in which X is >C═O, n is 1 and Y is H.

5. An N-2-hydroxypropyl piperidine according to claim 1 in which X is

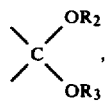

n is 1, and Y is H.

6. An N-2-hydroxypropyl piperidine according to claim 1 in which X is

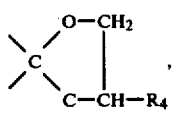

n is 1 and Y is H.

7. An N-2-hydroxypropyl piperidine according to claim 1 in which X is

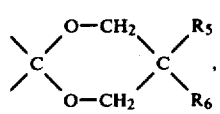

n is 1 and Y is H.

8. An N-2-hydroxypropyl piperidine according to claim 1 in which X is —CH$_2$—O—R$_1$, n is 1 and Y is H.

9. An N-2-hydroxypropyl piperidine according to claim 1 in which X is >CH$_2$OH, n is 1 and Y is

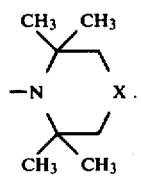

10. An N-2-hydroxypropyl piperidine according to claim 1 in which X is >CH$_2$, n is 1, and Y is

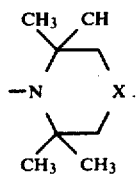

11. An N-2-hydroxypropyl piperidine according to claim 10 in which X is >C═O, n is 1 and Y is

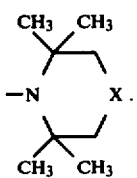

12. An N-2-hydroxypropyl piperidine according to claim 1 in which X is

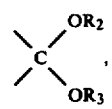

n is 1, and Y is

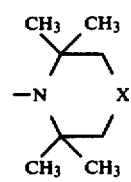

13. An N-2-hydroxypropyl piperidine according to claim 1 in which X is

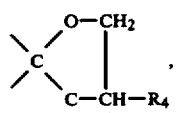

n is 1 and Y is

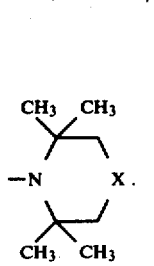

14. An N-2-hydroxypropyl piperidine according to claim 1 in which X is

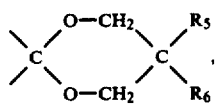

n is 1 and Y is

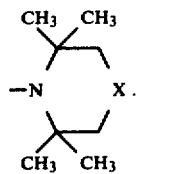

15. An N-2-hydroxypropyl piperidine according to claim 1 in which X is —CH$_2$—O—R$_1$, n is 1 and Y is

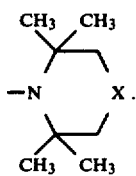

16. An N-2-hydroxypropyl piperidine according to claim 1 in which X is >CH$_2$OH, n is 2 and Y is oxyoxygen.

17. An N-2-hydroxypropyl piperidine according to claim 1 in which X is >CH$_2$, n is 2 and Y is oxyoxygen.

18. An N-2-hydroxypropyl piperidine according to claim 17 in which X is >C=O, n is 2 and Y is oxyoxygen.

19. An N-2-hydroxypropyl piperidine according to claim 1 in which X is

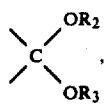

n is 2, and Y is oxyoxygen.

20. An N-2-hydroxypropyl piperidine according to claim 1 in which X is

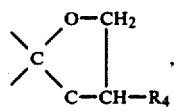

n is 2 and Y is oxyoxygen.

21. An N-2-hydroxypropyl piperidine according to claim 1 in which X is

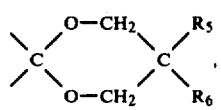

n is 2 and Y is oxyoxygen.

22. An N-2-hydroxypropyl piperidine according to claim 1 in which X is —CH$_2$—O—R$_1$, n is 2 and Y is oxyoxygen.

23. An N-2-hydroxypropyl piperidine according to claim 1 in which the compound is

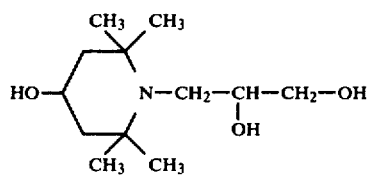

24. An N-2-hydroxypropyl piperidine according to claim 1 in which the compound is 25. An N-2-hydroxypropyl piperidine according to claim 1 in which the compound is

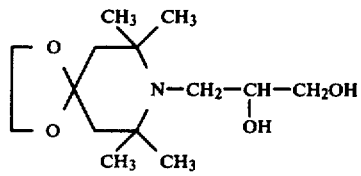

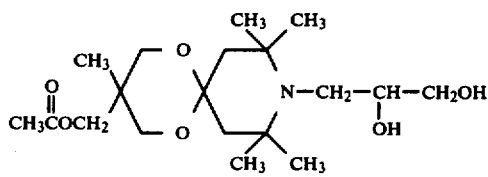

26. An N-2-hydroxypropyl piperidine according to claim 1 in which the compound is

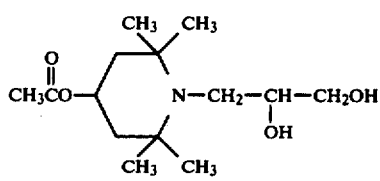

27. An N-2-hydroxypropyl piperidine according to claim 1 in which the compound is

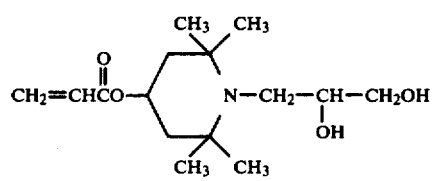

28. A stabilizer composition for improving resistance of olefin polymers to deterioration by heat and light comprising an N-2-hydroxypropyl piperidine according to claim 1 and a phenolic antioxidant having at least one phenolic hydroxyl group, at least one phenolic nucleus, and from about eight to about three hundred carbon atoms.

29. A stabilizer composition according to claim 28 in which the phenolic antioxidant has the formula:

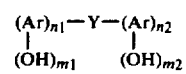

wherein
Y is a polyvalent linking group selected from the group consisting of oxygen; carbonyl; sulfur; sulfinyl; aromatic, aliphatic and cycloaliphatic hydrocarbon groups, and oxyhydrocarbon, thiohydrocarbon and heterocyclic groups having from one up to twenty carbon atoms;
Ar is a phenolic nucleus containing at least one free phenolic hydroxyl group up to a total of five;
m$_1$ and m$_2$ are numbers from one to five, and
n$_1$ and n$_2$ are numbers from one to four.

30. An olefin polymer composition having improved resistance to deterioration by light comprising an olefin polymer selected from the group consisting of polymers of alpha-olefins having from two to six carbon atoms and polystyrene, and an amount to enhance the resistance of the polymer to deterioration of an N-2-hydroxypropyl piperidine compound in accordance with claim 1.

31. An olefin polymer composition in accordance with claim 30 wherein the polyolefin is polypropylene.

32. An olefin polymer composition in accordance with claim 30 wherein the polyolefin is polyethylene.

33. An olefin polymer composition having improved resistance to deterioration by heat and light comprising an olefin polymer selected from the group consisting of polymers of alpha-olefins having from two to six carbon atoms and polystyrene, and an amount to enhance the resistance of the polymer to deterioration by heat and light of a stabilizer composition in accordance with claim 28.

34. An olefin polymer composition in accordance with claim 33 wherein the polyolefin is polypropylene.

35. An olefin polymer composition in accordance with claim 28 wherein the polyolefin is polyethylene.

* * * * *